(12) United States Patent
Dasari et al.

(10) Patent No.: US 11,247,964 B2
(45) Date of Patent: Feb. 15, 2022

(54) METHOD OF PROCESSING PHOSPHOLIPID BASED LIPID MATERIALS

(71) Applicant: RRIP, LLC, Pleasant Hill, IA (US)

(72) Inventors: Mohan Prasad A. Dasari, West Des Moines, IA (US); Abdullah A. Mahfuz, Johnston, IA (US); Shashank Ravi, Des Moines, IA (US); Hugh Tallant Warren, Des Moines, IA (US)

(73) Assignee: RRIP, LLC, Pleasant Hill, IA (US)

(*) Notice: Subject to any disclaimer, the term of this patent is extended or adjusted under 35 U.S.C. 154(b) by 1102 days.

(21) Appl. No.: 15/131,133

(22) Filed: Apr. 18, 2016

(65) Prior Publication Data

US 2016/0229793 A1    Aug. 11, 2016

Related U.S. Application Data

(63) Continuation-in-part of application No. 12/771,725, filed on Apr. 30, 2010, now Pat. No. 9,315,764.

(51) Int. Cl.

| | | |
|---|---|---|
| *C07C 227/40* | (2006.01) | |
| *C07C 227/28* | (2006.01) | |
| *C07C 213/08* | (2006.01) | |
| *C07C 213/10* | (2006.01) | |
| *C07C 29/09* | (2006.01) | |
| *C07C 29/76* | (2006.01) | |
| *A23K 20/174* | (2016.01) | |
| *C11B 13/02* | (2006.01) | |
| *A23K 10/14* | (2016.01) | |
| *A23K 20/158* | (2016.01) | |
| *A23K 20/26* | (2016.01) | |
| *C11B 13/00* | (2006.01) | |
| *A23J 7/00* | (2006.01) | |
| *C12P 7/64* | (2006.01) | |
| *C11B 11/00* | (2006.01) | |
| *C07C 227/38* | (2006.01) | |
| *C11B 1/02* | (2006.01) | |

(52) U.S. Cl.
CPC .............. *C07C 227/28* (2013.01); *A23J 7/00* (2013.01); *A23K 10/14* (2016.05); *A23K 20/158* (2016.05); *A23K 20/174* (2016.05); *A23K 20/26* (2016.05); *C07C 29/095* (2013.01); *C07C 29/76* (2013.01); *C07C 213/08* (2013.01); *C07C 213/10* (2013.01); *C07C 227/38* (2013.01); *C07C 227/40* (2013.01); *C11B 11/00* (2013.01); *C11B 13/00* (2013.01); *C11B 13/02* (2013.01); *C12P 7/64* (2013.01); *C11B 1/025* (2013.01); *Y02W 30/74* (2015.05)

(58) Field of Classification Search
CPC ... C07C 227/28; C07C 227/38; C07C 227/40; C07C 29/09; C07C 213/08; C07C 213/10; C07C 29/095; A23J 7/00; C11B 9/02
See application file for complete search history.

(56) References Cited

U.S. PATENT DOCUMENTS

| | | | |
|---|---|---|---|
| 4,698,185 A * | 10/1987 | Dijkstra | C11B 3/06 554/176 |
| 5,703,255 A | 12/1997 | Weete et al. | |
| 5,833,858 A | 11/1998 | Umeda et al. | |
| 5,955,327 A * | 9/1999 | Hirai | C12P 13/00 435/128 |
| 6,001,640 A | 12/1999 | Loeffler et al. | |
| 6,140,519 A | 10/2000 | Hutton et al. | |
| 6,399,802 B2 * | 6/2002 | Reaney | C11B 13/02 554/177 |
| 7,465,717 B2 | 12/2008 | Dexter et al. | |
| 7,566,570 B2 | 7/2009 | Abril | |
| 7,696,369 B2 | 4/2010 | Kellens et al. | |
| 8,232,418 B1 | 7/2012 | Bilbie et al. | |
| 8,460,905 B2 | 6/2013 | Dayton et al. | |
| 8,648,210 B2 | 2/2014 | Hujanen et al. | |
| 8,845,765 B2 | 9/2014 | Malm et al. | |
| 8,956,853 B2 | 2/2015 | Dayton et al. | |
| 2006/0030012 A1 * | 2/2006 | Kellens | A23J 7/00 435/134 |
| 2014/0135515 A1 * | 5/2014 | Dasari | C11B 3/04 554/212 |
| 2014/0371476 A1 | 12/2014 | Dayton et al. | |
| 2017/0311632 A1 * | 11/2017 | Yang | A23L 29/231 |

OTHER PUBLICATIONS

Dowd, JAOCS, 73(10): 1287-1295, 1996. (Year: 1996).*
Nieuwenhuyzen et al., Eur. J. Lipid Sci. Technol., 2008, 110:472-486 (Year: 2008).*

* cited by examiner

*Primary Examiner* — Allison M Fox
*Assistant Examiner* — Qing Xu
(74) *Attorney, Agent, or Firm* — Brick Gentry PC; Brian J. Laurenzo; Jessica L. Susie

(57) ABSTRACT

The present invention provides methods of processing lipid materials such as soapstock, wet gums and dry gums. Enzymes are utilized to catalyze hydrolysis of the lipids materials to recover fatty acids. Addition of organic acids and/or polyols improved yield of fatty acids and reduced formation of emulsion. Lipid materials can be formulated with other agricultural products as new value-added animal feed products. Further, a process for concentrating nitrogenous compounds such as choline, inositol, ethanolamine and serine from phospholipid materials obtained as byproducts from vegetable oil refining is provided. The process involves performing hydrolysis of the gum based products in the presence of an alcoholic solvent and acid catalyst. Post hydrolysis, gums breakdown to oil and water phases which are further separated and concentrated. These concentrated products may be further fractionated to concentrate individual nitrogenous compounds.

18 Claims, 1 Drawing Sheet

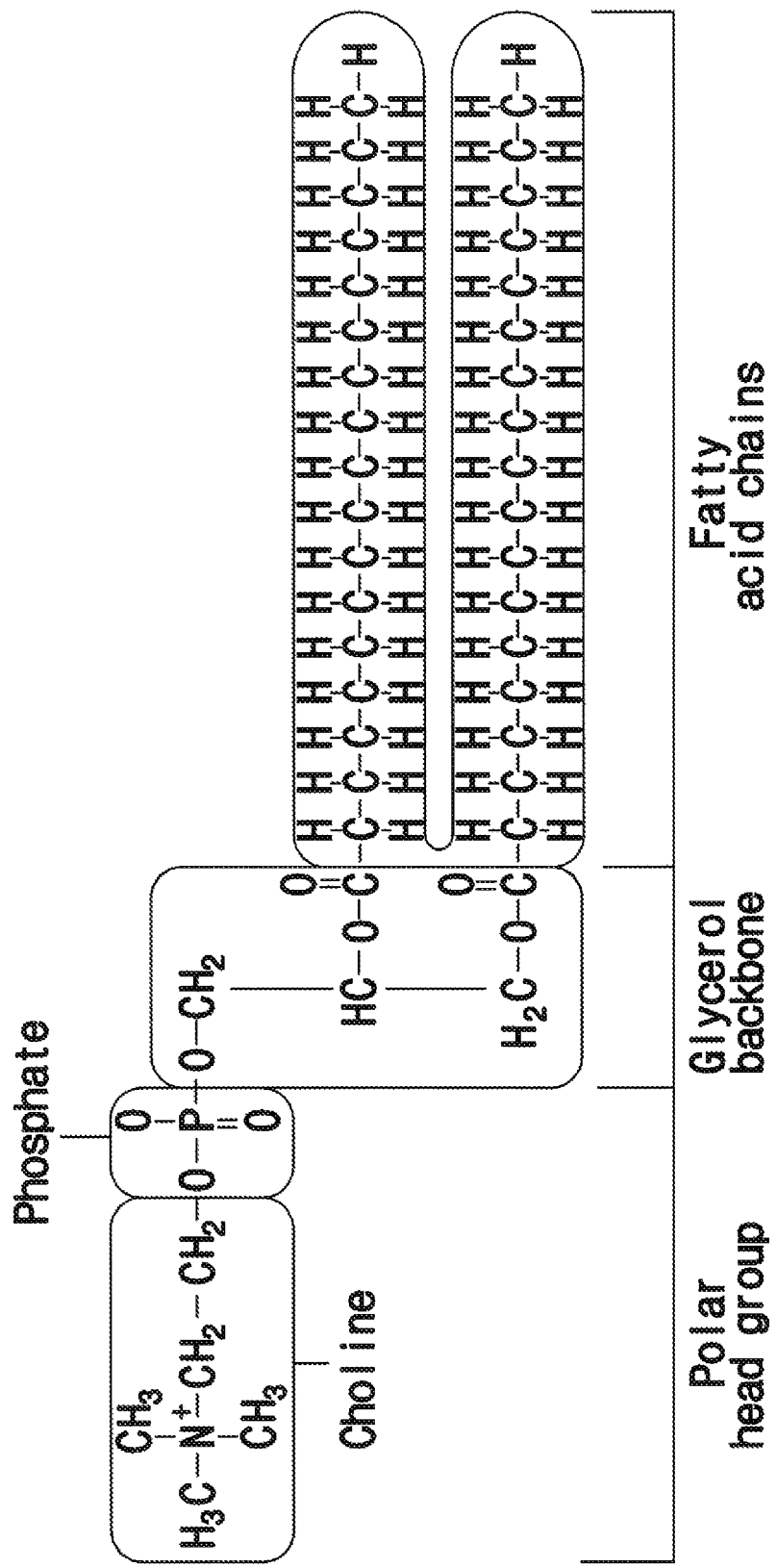

METHOD OF PROCESSING PHOSPHOLIPID BASED LIPID MATERIALS

CROSS-REFERENCE TO RELATED APPLICATIONS

This application is a continuation-in-part of U.S. non-provisional patent application Ser. No. 12/771,725, filed on Apr. 30, 2010 and entitled "Method of Processing Phospholipid Based Lipid Materials", which claims the benefit of U.S. provisional patent application Ser. No. 61/174,731, filed May 1, 2009, and entitled "Enzymatic Processing of Lipid Materials". Both application Ser. No. 12/771,725 and 61/174,731 are hereby incorporated by reference in their entireties.

BACKGROUND OF THE INVENTION

Field of the Invention

This invention relates to the field of chemical processing, and more particularly to processing crude vegetable oil, as well as methods for processing nitrogen-based materials from gums and resulting products associated therewith.

Description of the Related Art

Crude vegetable oils predominantly contain triglycerides along with some impurities such as free fatty acids (sometimes "free fatty acids" or "FFA"), phospholipids, etc. These impurities are typically removed from crude oil by the vegetable oil refining process. Therefore, vegetable oil refining yields byproducts which may be further processed into valuable products. These byproducts include wet gums, soapstocks, dried gums, vegetable oil phospholipids (VOP), lecithin, and others. As is known in the art, wet gums may be enzymatic wet gums or wet gums derived from other degumming processes. To that end, the first step in the refining process is degumming. One method of degumming is where the oil may be treated with aqueous acid solution to remove both hydratable and non-hydratable phospholipids. These phospholipids are separated from the oil by centrifugation and are commonly known as wet gums. Wet-gum is a dark brown to blackish in color, highly viscous product comprising of phosphatides, water, triglycerides, and free fatty acids. In addition to the above processes, vegetable oil refining facilities also refine and degum the vegetable oil using enzymes. One byproduct of these processes is enzymatic wet gums. Furthermore, other degumming processes include, but are not limited to, water degumming and high shear degumming.

The degummed oil may then be treated with aqueous alkali (typically sodium or potassium hydroxide) in order to remove the free fatty acids. The alkali reacts with the free fatty acids present in the crude glycerides to form soap. The soap and other solid impurities are separated from the refined oil by centrifuging and are generally known as "soapstock" or "foots". The soapstock obtained from this process is known as degummed soapstock and typically contains vegetable oil, water, soap, and traces of phospholipids. Alternately, in some current oil refineries the phospholipids and soapstock are removed simultaneously. The soapstock from this alternate process is known as gummed soapstock and typically contain vegetable oil, phospholipids, water and soap. Soapstock is alkaline in nature due to the presence of unreacted alkali. The refined oil is further processed.

As is known in the art, gums include phospholipids. These phospholipids may include, but are not limited to, phosphatidyl choline, phosphatidyl ethanolamine, phosphatidyl inositol, and phosphatidic acid. These compounds may be particularly valuable as nutraceutical materials, which may be beneficial as-is or may be further processed for consumption. Furthermore, the nutraceutical properties may be beneficial for humans and animals. Each of these degumming methods produces a variety of byproducts. These byproducts, depending on the degumming method, comprise of phospholipids, moisture, triglycerides, free fatty acids, salts, glycolipids, etc. Lecithin, VOP, dried gums, wet gums, and enzymatic wet gums are some of the commercially available byproducts. Lecithin, VOP, and enzymatic wet gums are exemplary byproducts that are evaluated in connection with the present invention. Table 1 below shows the composition of sample byproducts. These materials differ in the common components such as oil content, FFA content, moisture content and phospholipid content.

TABLE 1

Component analyses on Feed stocks including lecithin, VOP, wet gums obtained from a high shear process, wet gums from a first vendor obtained from an enzymatic process, and wet gums from a second vendor obtained from an enzymatic process

|  | Lecithin (as-is) | VOP (as-is) | Wet Gums from high shear process (as-is) | Vendor 1 Wet Gums Enzymatic process (as-is) | Vendor 2 Wet Gums Enzymatic process (as-is) |
|---|---|---|---|---|---|
| Moisture | 0-1% | 2-8% | 25-40% | 45-55% | 43.5% |
| Neutral Oil | 26-29% | 29-38% | 10-25% | 17-18% | 9.83% |
| HA | 2-4% | 9-15% | 0.5-5% | 1-2% | 5.22% |
| AI | 65-69% | 44-55% | 40-55% | 28-30% | 38.98% |
| HI | 0-1% | 2-8% | 2-10% | 3-4% | 25.31% |
| AI-HI | 65-69% | 36-53% | 30-55% | 25-28% | 13.67% |

Additionally, both wet gums and soapstock have commercial value as a source of fatty acids. Fatty acids can be recovered from wet gums and soapstock by hydrolysis. Wet gums are currently being sold as a raw material for lecithin production and for animal feed blending. The wet gums can be dried using an evaporator to a low moisture product known as dry gums. The wet gums and dry gums products, although nutritionally desirable and abundantly available in the market, find limited application in feed due to their handling and storage difficulties.

Turning again to the hydrolysis reaction to recover fatty acids from wet gums and soapstock, this reaction may be carried out in a variety of ways. As described in detail herein, enzymes may be used. Moreover, physical methods may be used. The hydrolysis reaction results in at least two phases, a fatty-acid-rich oil phase and a water phase. An emulsion phase may also result, although methods described herein may minimize or eliminate such a phase. The fatty-acid-rich oil phase contains valuable products, including but not limited to oil and fatty acids. Moreover, the water phase may contain valuable products. Namely, as wet gums are hydrolyzed, water soluble components of the phospholipids are present in the water phase, including but not limited to phosphatidylcholine, phosphatidyl ethanolamine, phosphatidyl inositol, and phosphatidic acid. As discussed hereinbelow, those components are valuable and may be further processed to split the nitrogen-based compound from the phosphate group and concentrate the nitrogen-based compound.

In one example, wet-gums contain phospholipids, such as phosphatidylcholine, which is necessary for mobilization of fat out of the liver and also improves breeding performance, milk production, and fetal growth of an animal. Therefore, choline is known to be beneficial in animal feed. Currently, synthetic choline is added to animal feed as a supplement. Synthetic choline is manufactured from petroleum. A natural source of choline is the gums, including enzymatic wet gums, obtained as a byproduct of vegetable oil refining. Therefore, there exists a need in the art for efficient methods to process enzymatic wet gums to obtain choline-containing compounds and/or concentrated choline for use in animal feed and supplements. There further exists a need for methods and products to effectively deliver the choline-containing compounds and/or concentrated choline to animals for consumption.

Amongst these feed stocks, Lecithin has the highest total choline content in as-is basis and wet gums in dried basis, estimated by calculating the choline in PC, LPC and GPC compositions in feed stocks. The phospholipid/choline content on feed stocks and product phases were determined using 31P NMR method. AI-HI wet chemistry method and Choline chloride method (AOAC 999.14).

TABLE 2

Choline content in different Feed stocks

| Feed Stock | PC % | LPC % | GPC % | Phosphocholine % | Choline content % |
|---|---|---|---|---|---|
| Lecithin | 21.3 | 0.46 | 0.16 | ND | 2.88 |
| VOP | 5.97 | 4.96 | 1.47 | ND | 2.43 |
| 2G Enzymatic Wet Gums (dried) | 2.29 | 2.83 | 1.23 | ND | 3.25 |
| 3G Enzymatic Wet Gums | ND | 0.2 | 0.09 | 4.03 | 2.3 |

TABLE 3

Inositol content in different Feed stocks

| Feed Stock | PI % | LPI % | GPI % | Inositol content % |
|---|---|---|---|---|
| Lecithin | 12.27 | 0 | 0 | 2.65 |
| VOP | 2.4 | 2.2 | 0 | 1.21 |
| 2G Enzymatic Wet Gums (dried) | 5 | 3 | 0 | 2.03 |
| 3G Enzymatic Wet Gums | ND | ND | 0.08 | 0.08 |

TABLE 4

Ethanolamine content in different Feed stocks

| Feed Stock | PE % | LPE % | GPE % | Ethanolamine content % |
|---|---|---|---|---|
| Lecithin | 18.63 | 0.42 | 0 | 4.02 |
| VOP | 4.5 | 2.8 | 0 | 1.85 |
| 2G Enzymatic Wet Gums (dried) | 4.7 | 6.1 | 0 | 1.94 |
| 3G Enzymatic Wet Gums | ND | 0.96 | ND | 0.96 |

Turning again to the soapstock, fatty acids can be recovered from soapstock as a valuable product. A product high in fatty acid content (generally about 55-65% free fatty acids) is obtained from the soapstock by acidulation with a mineral acid such as sulfuric or hydrochloric acid. The conventional way of acidulating soapstock is to react it with acid solution at an elevated temperature under continuous agitation. The gummed soapstock typically contains considerable amounts of phospholipids (gums) which act as emulsifiers, for which reason a very long settling time may also be necessary to get acid oil of acceptable purity. If the acidulated soapstock is allowed to settle, it separates into three layers.

The bottom layer is an acidic aqueous solution which can be pumped off and recycled. The top layer is the desired fatty acid product, known as acid oil, which may be used as is (e.g., for animal feed), or may be further treated to obtain more highly purified fatty acids (e.g., by distillation). The middle layer is an emulsified sludge material, a semisolid, emulsified layer containing primarily phospholipids, water, and a substantial quantity of the desired fatty acid product entrained therein. With the soapstock containing large amounts of gums and impurities, it is often difficult to obtain a complete separation of the phases which give rise to considerable amount of emulsion layer resulting in significant loss of the acid oil. Also, due to the corrosive nature of the sulfuric acid and the acidulated water the necessary protection against the corrosion make relatively simple equipment rather expensive and the maintenance costs are often considerable.

As a consequence of the foregoing situation, there has existed a longstanding need for a new and improved method of processing crude vegetable oils and the provision of such a method is a stated objective of the present invention.

BRIEF SUMMARY OF THE INVENTION

Briefly stated, the present invention provides a method utilizing enzymes to catalyze the soapstock acidulation process, and methods of processing wet and dry gums as feed stock to produce acid oil, and to formulate new value-added animal feed products.

An objective of this invention is to utilize enzymes such as protease, lipase, phospholipase, etc., to catalyze the soapstock acidulation reaction.

Both wet gums and dry gums have high fatty acid content, as compared to soapstock, and can be used as an alternate feedstock for producing fatty acids in high yields. Another method of invention is to research and develop novel methods to process both wet and dry gums as new source of feed stock to produce acid oil or to develop new value-added products.

Also provided is a method of concentrating nitrogen-based material from phospholipid materials comprising suspending the nitrogen-based material in oil and mixing the phospholipid materials and oil with a fluidizer and an alkali to create a first mixture. The fluidizer may be glycerol. Furthermore, the first mixture may be homogenized. The homogenized mixture may settle into a first phase and a second phase. The first phase may comprise nitrogen-based material, which may include choline, ethanolamine, serine, inositol, and combinations thereof.

Further provided is a method of processing a feedstock including at least one phospholipid material comprising hydrolyzing the feedstock with a catalyst, for example an enzyme or acid such as sulfuric acid, to form first and second phases. The first phase comprises oil, while the second phase comprises phospholipid material containing at least one nitrogen-based material. The nitrogen-based material may then be concentrated. The hydrolysis may take place in the presence of an alcoholic solvent, which may be selected form the group consisting of methanol, ethanol, and isopropanol. Accordingly, the first phase may further comprise alcohol, while the second phase may further comprise water and alcohol. The water and alcohol may be separated from the second phase prior to the concentrating step, such as by drying. The nitrogen-based material may be fractionated. Moreover, the second phase may be treated with alcohol to form an alcohol phase and a residue phase. The alcohol phase may be filtered, such as with filter paper, to create a permeate and a retentate. Nitrogen-based material may be concentrated from at least one of the permeate and the retentate.

Also provided is a method of concentrating nitrogen-based material from phospholipid materials comprising mixing the phospholipid materials with an oil and a fluidizer. Further added to the mixture is an alkali. The mixture may then be homogenized to create a first phase and a second phase. Nitrogen-based materials may be concentrated from the first phase.

BRIEF DESCRIPTION OF THE DRAWINGS

FIG. 1 is a diagram of an exemplary phospholipid molecule, specifically phosphatidyl choline.

DETAILED DESCRIPTION OF THE INVENTION

This invention describes the use of enzymes to catalyze the soapstock acidulation process, methods of processing feedstock of wet and dry gums to produce acid oil, and animal feed formulations utilizing wet and dry gums. Moreover, the invention describes further processing of wet and dry gums to obtain valuable products.

Overall objective of this study is to research and develop alternate methods to treat the vegetable oil refining by products i.e., soapstock, wet gums, dry gums. One of the methods of invention is to utilize enzymes such as protease, lipase, phospholipase, etc., to catalyze the soapstock acidulation reaction. Following are the advantages of the enzymatic processing of current invention over the conventional acidulation process.

1. The enzymes are used to convert the soap into free fatty acids and are further used to hydrolyze the gums (phospholipids) into free fatty acids and corresponding phosphatide molecules. This results in little or no formation of middle emulsion layer, after settling thereby eliminating the loss of acid oil through the emulsion layer.

2. The enzymes are usually very active at a neutral pH range and hence the reaction is conducted at a pH range of about 6-7 as compared to the usual acidulation pH of 1.5-2. This reduces the usage of sulfuric acid and makes this a very environmentally friendly, green process.

3. In the conventional process there is a high chance for degradation of neutral oil and other lipid components as a result of oxidation at the acidic process conditions. In the enzymatic process, the acid oil produced will have a higher quality viz. (a) higher neutral oil content (b) lighter golden-brown color (c) higher oxidative stability (d) higher amount of nutraceuticals such as sterols, tocopherols, etc.

4. The acid water generated in conventional process has a pH in the range of 1-1.5 and it has to be further neutralized with caustic for safer handling and disposal. The resultant water from the enzymatic process will be at a neutral pH range and hence does not have to be neutralized.

5. In the enzymatic process, a centrifuge system can be used to separate the individual components of acidulated soapstock. This option is fairly limited in the conventional process due to the low process pH. Utilizing a centrifuge for separation, instead of gravitational settling, will tremendously reduce the process time, and also help extract most of the oil from the emulsion phase.

TABLE 5

Comparison of Conventional Process and Enzymatic Process

| Conventional Process | Enzymatic Process |
| --- | --- |
| 1. Low pH process-typically 1.5 to 2 pH | Higher pH-typically in the neutral pH range |
| 2. Primarily hydrolyzes soap | Hydrolyzes soap as well as phospholipids |
| 3. More emulsion layer | Little or no emulsion layers |
| 4. Oil yield loss through emulsion layer | Reduced oil loss |
| 5. Corrosive process | Green process |
| 6. Low neutral oil in the final product | Higher neutral oil |
| 7. Dark brown-black color of oil | Lighter golden-brown color |
| 8. Oil is susceptible for oxidation | Higher oxidative stability |
| 9. High degradation sterols and tocopherols | Less degradation of sterols and tocopherols |
| 10. Acid water needs neutralization for disposal | No treatment of Water is necessary |
| 11. Centrifuge cannot be used for separation-low pH | Centrifuge can be used for separation |

Materials and Methods

The soapstocks used in this study are obtained by alkali refining of degummed or gummed vegetable oil from three different vegetable oil refineries.

TABLE 6

Soapstock Analysis

| Soapstock | TFA Range (%) | Moisture Range (%) | Phospholipids Range (%) | pH Range (%) |
|---|---|---|---|---|
| Soapstock A | 15-40 | 45-70 | 5-10 | 8-10 |
| Soapstock B | 15-40 | 40-70 | 5-10 | 8-10 |
| Soapstock C | 15-55 | 30-75 | 0-2 | 6-8 |

Moisture of the soapstock was adjusted to 70% for better mixing

A 40 g sample of soapstock was heated to 80° C., stirred at approximately 100 rpm while concentrated sulfuric acid was slowly added. Ten minutes of blending time is allowed between each acid addition and pH measurement. Upon reaching a desired of pH (<2), the moisture was allowed to settle in an 80° C. oven for eight hours. After settling, the oil, water and emulsion fractions/layers were measured and then the sample is centrifuged at 3000 RCF for three minutes to record the changes between separation techniques.

A 40 g sample of soapstock was heated at 55° C. and started stirring at approximately 100 rpm. As needed, pH of the soapstock is adjusted to the working pH of the enzyme. Upon reaching a desired pH, enzyme was added at 2% concentration of the soapstock (db). The reaction mixture was incubated for two hours and then settled in an 80° C. oven for eight hours. After settling, the individual fractions/layers were measured and then the sample was centrifuged at 3000 RCF for three minutes to record the changes between separation techniques. A blank experiment (as −ve control) was run without using an enzyme. Table 1A shows the list of enzymes and their average working pH.

TABLE 7

List of enzymes, their types and average working pH used in this study.

| Enzyme type | Optimal pH range | Average working pH |
|---|---|---|
| Phospholipase A1 | 5.0-5.5 | 5.0 |
| Phospholipase A2 | 5.0-8.0 | 7.0 |
| Phospholipase C | 6.0-7.5 | 7.0 |
| Lipase | 5.0-5.5 | 5.0 |
| Protease | 7.0-10 | 7.0 |

Calculations:

% Oil=volume of oil/total total volume×100

% Emulsion=volume of Emulsion/total volume×100

% Water=volume of Water/total volume×100

Results

Soapstock A (53% moisture, 32% TFA and 6.4% phospholipids)

TABLE 8

Results

| | | Treatment pH | Settling for 8 hours | | | Centrifugation | | |
|---|---|---|---|---|---|---|---|---|
| No | Enzyme | | Oil % | Emulsion % | Water % | Oil % | Emulsion % | Water % |
| 1 | +ve control | 1.25 | 32 | 16 | 52 | 36 | 7 | 57 |
| 2 | −ve control | 5.74 | no separation | | 23 | 77 | none | |
| 3 | Phospholipase A1 | 5.74 | 32 | 2 | 67 | 32 | 2 | 66 |
| 4 | Phospholipase A2 | 6.30 | 33 | 13 | 54 | 36 | 0.6 | 64 |
| 5 | Phospholipase C | 6.17 | 9 | 21 | 70 | 17 | 3 | 80 |
| 6 | Lipase | 5.2 | 21 | 11 | 68 | 24 | 7 | 68 |
| 7 | Protease | 6.17 | Oil & Emulsion mixed | | 67 | 14 | 19 | 67 |

Based on above table, it can be stated that phospholipase A2 and phospholipase A1 will work on soapstock hydrolysis. Enzymatic treatment improved oil yield and decreased the emulsion layer. It was also observed that the color of the oil and water is lighter than the positive control. It was also observed that centrifugation of the reaction mixture resulted in a better oil yield.

In this study, the treatment conditions were controlled in order to compare between an untreated and treated sample. Therefore, the treatment condition should not be considered as optimal condition for the above listed enzymes.

Soapstock B (53% moisture, 25% TFA and 0.3% phospholipids)

TABLE 9

Results

| | | Treatment pH | Settling for 8 hours | | | Centrifugation | | |
|---|---|---|---|---|---|---|---|---|
| No | Enzyme | | Oil % | Emulsion % | Water % | Oil % | Emulsion % | Water % |
| 1 | +ve control | 1.70 | 24 | 6 | 70 | 28 | 2 | 70 |
| 2 | −ve control | 6.74 | Oil & Emulsion | | 62 | Oil & Emulsion | | 62 |

TABLE 9-continued

| | | Treat-ment pH | Settling for 8 hours | | | Centrifugation | | |
|---|---|---|---|---|---|---|---|---|
| No | Enzyme | | Oil % | Emulsion % | Water % | Oil % | Emulsion % | Water % |
| 3 | Phospholipase A1 | 5.12 | Oil & Emulsion | | 67 | 29 | 4 | 67 |
| 4 | Phospholipase A2 | 6.74 | Oil & Emulsion | | 66 | 31 | 4 | 66 |
| 5 | Phospholipase C | 6.74 | Oil & Emulsion | | 54 | 31 | 4 | 65 |
| 6 | Lipase | 6.05 | Oil & Emulsion | | | Oil & Emulsion | | |
| 7 | Protease | 6.74 | 31 | 13 | 56 | 32 | 1 | 67 |

A variety of enzymes including protease seemed to work on soapstock B. Enzymatic treatment yielded more oil than the positive control. The viscosity of the oil from enzymatic treatment is lower than negative control but higher than the positive control. The higher viscosity is due to suspended water and gums in the oil phase. At higher pH, water and gums may get trapped in the oil phase making it difficult to separate. The reaction conditions may have to be optimized in order to facilitate better separation of the layers.

Soapstock C (52.9% moisture, 29.2% TFA and 5.4% phospholipids)

TABLE 10

| | | Treat-ment pH | Settling for 8 hours | | | Centrifugation | | |
|---|---|---|---|---|---|---|---|---|
| No | Enzyme | | Oil % | Emulsion % | Water % | Oil % | Emulsion % | Water % |
| 1 | +ve control | 1.14 | Very little oil separation | | | 23 | 19 | 58 |
| 2 | −ve control | 6.91 | 14 | 38 | 48 | 21 | 23 | 56 |
| 3 | Phospholipase A1 | 5.09 | 29 | 14 | 57 | 25 | 8 | 67 |
| 4 | Phospholipase A2 | 6.91 | 18 | 21 | 61 | 24 | 12 | 64 |
| 5 | Phospholipase C | 6.91 | Oil & Emulsion mixed | | | Oil & Emulsion mixed | | |
| 6 | Lipase | 5.09 | 29 | 6 | 65 | 28 | 5 | 67 |
| 7 | Protease | 6.91 | Oil & Emulsion | | | Oil & Emulsion Mixed | | |

Based on enzymatic treatment on soapstock C, it was observed that lipase, phospholipase AI and phospholipase A2 worked better.

Materials and Methods:

Wet-gum and dry gum samples were obtained from two different vegetable oil refineries. Typical composition of all of gum materials used in this study are shown in Table 1. The wet gum sample was kept in refrigerator until used and were thawed for about 30 minutes, mixed thoroughly and then samples were collected for analysis and experiments.

TABLE 11

Analysis of various gum samples

| Component | Wet gums | Dry gums |
|---|---|---|
| Oil (%) | 10-25 | 25-35 |
| Free Fatty Acids (%) | 0.5-5 | 10-15 |
| Acetone Insolubles (%) | 40-55 | 50-60 |
| Phospholipids (%) | 30-55 | 40-50 |
| Moisture (%) | 25-40 | 1-5 |
| Total Fatty Acids (%) | 35-50 | 60-70 |

Wet gums and dry gums are highly viscous and create a major issue during the treatment/processing. The viscosity of the gum slightly reduces with increase in the temperature. However, as the temperature is increased further, the gum starts to lose moisture and begin to coagulate. Addition of water to the wet did not reduce the viscosity to a great extent. Therefore, an ideal solvent will reduce the viscosity of the wet gums, does not interfere in the reaction (stable), less volatile, cheap and has low solubility in the oil phase. Glycerin was considered as a solvent because it satisfies our requirements and it is also available in abundance as a by-product of biodiesel industry.

TABLE 12

Effect of glycerin addition on viscosity of wet gums

| Amount of 50% glycerin | Viscosity Range, SSU |
|---|---|
| 40% | 3,000-5,000 |
| 20% | 15,000-20,000 |
| 10% | 15,000-20,000 |
| 5% | 30,000-40,000 |
| 0% | 40,000-50,000 |

Based on above study, it was observed that addition of glycerin reduced the viscosity of wet gums and increased the flowability and mixing capability at 80° C. temperature. It was also observed that 50% diluted glycerin performed more effectively than concentrated glycerin. Glycerin was also able to reduce the viscosity of dry gums as well.

Results and Discussion:

Several options were evaluated to process the gum type materials. Out of the available options, on basis of their feasibility, four options were chosen to be studied further.

A. Option 1: Enzymatic Hydrolysis of gums
B. Option 2: Chemical Hydrolysis of gums
C. Option 3: Liquid feed/mold inhibitor product by combining with organic acids
D. Option 4: Dry feed product by combining with agricultural co-products Each option is described separately in the following pages A. Option 1: Enzymatic Hydrolysis of Gums Wet gum was treated with enzymes such as Phospholipase AI, Phospholipase A2, and Phospholipase C for 20 hours at 50° C. and pH at around 6. Higher amount of enzyme was used in order to evaluate the efficacy of the enzyme for the hydrolysis reaction. Once the enzymes are identified, the conditions can be further optimized in order to make it feasible for the commercial scale production. Among these enzymes. Phospholipase A2 and Phospholipase C were more effective. They released more clear oil with some amount of middle emulsion phase still existing. Other enzymes showed same result as a negative control (data not shown). Subsequently, some other experiments were carried out using Phospholipase A2 enzyme and other combinations like glycerin, acid oil as solvent. pH of the wet gums was adjusted to desired pH with NaOH. The reaction was carried out at 45-50° C. with constant stirring. After 20 hours reaction the sample was heated to 90° C.-95° C. in an oven for 10 minutes to inactivate the enzyme and then transferred to a centrifuge tube followed by centrifugation at 3000 rpm for three minutes.

TABLE 13

Results of enzymatic hydrolysis of wet gums

| No | Treatment | Treatment pH | Oil yield, g | Oil yield, % |
|---|---|---|---|---|
| 1 | 100 g Wet gums (Control) | 5.8 | 0 | 0 |
| 2 | 100 g Wet gums + 0.25% Phospholipase A2 | 7 | 17 | 43 |
| 3 | 100 g Wet gums + 2% Phospholipase A2 | 5.8 | 30 | 75 |
| 4 | 100 g Wet gums + 20 g glycerin (Control) | 5.3 | 0 | 0 |
| 5 | 100 g Wet gums + 20 g glycerin + 0.5% | 5.4 | 29 | 73 |
| 6 | 100 g Wet gums + 16 g water + 0.5% Phospholipase | 5.2 | 20 | 50 |

Based on the results in Table 3, it can be concluded that, due to high viscosity of the gums, enzyme Phospholipase A2 alone may be able to hydrolyze the wet gums. Addition of water, fusel oil, isopropanol and propylene glycol (data not shown) to wet gums showed a slight increase on the oil but no water was separated. On the other hand, when wet gum was mixed with acid oil and glycerin the viscosity was reduced facilitating the enzymatic reaction.

Dry gum pH was adjusted using 4M NaOH. The reaction was carried out at 45° C. for Phospholipase A2 and 60° C. for Phospholipase C with constant stirring for 20 hrs. Once incubation was done the emulsion was put in a 90° C. oven for 10 min to inactivate the enzyme and then centrifuged at 3000 rpm for three minutes. Table 4 shows the result of enzymatic treatment of dry gums. Phospholipase A2 yielded more oil than Phospholipase C at same enzyme concentration. A clear oil phase with a bottom emulsion layer was observed in all the cases.

TABLE 14

Enzymatic Hydrolysis of Dry Gums

| No | Treatment | Treatment pH | Oil yield, g | Oil yield, % |
|---|---|---|---|---|
| 1 | 100 g Dry gums (Control) | 5.9 | 6 | 10 |
| 2 | 100 g Dry gums + 0.5% Phospholipase A2 | 5.7 | 18 | 28 |
| 3 | 100 g Dry gums + 2% Phospholipase A2 | 5.9 | 51 | 81 |

TABLE 14-continued

Enzymatic Hydrolysis of Dry Gums

| No | Treatment | Treatment pH | Oil yield, g | Oil yield, % |
|---|---|---|---|---|
| 4 | 100 g Dry gums + 20 g glycerin + 1% Phospholipase | 5.3 | 19 | 30 |
| 5 | 100 g Dry gums + 20 g glycerin + 10 g water + 0.5% Phospholipase A2 | 5 | 33 | 52 |
| 6 | 100 g Dry gums + 100 g wet gums + 20 g glycerin 0.25% | 5.9 | 33 | 63 |
| 7 | 100 g Dry gums + 2% Phospholipase C | 6.7 | 34 | 54 |

B. Option 2: Chemical Hydrolysis of Gums

About 80 g of sample was heated to 80° C., mixed with a solvent as needed and stirred at approximately 100 rpm while concentrated sulfuric acid was slowly added. Ten minutes of blending time is allowed between each acid addition and pH measurements. Upon reaching a desired pH (<2), the mixture was settled in an 80° C. oven for eight hours.

Wet gum was mixed with various solvents and then hydrolyzed (Table 5). Among these solvents propionic acid gave the highest oil yield. The viscosity of wet gums significantly reduces when it is mixed with propionic acid. This indicated that most phospholipids are soluble in propionic acid facilitating the hydrolysis reaction. Addition of propionic acid as solvent, therefore, increased the oil yield and significantly reduced the emulsion yield. However, the addition of propionic acid significantly increased the moisture content of the oil as compared to the control. Propionic acid concentration from 10% and 5% resulted in 14.4% to 3.61% moisture content in the oil, respectively. Addition of 10% acetic acid as a solvent resulted in similar oil yield as well as lower moisture (4.6%) content in the oil phase. This indicates that the propionic acid, due to its intermediate polarity, has a tendency to act as a co-solvent for oil, water and phospholipids thereby dissolving some moisture and phospholipids in the oil phase. On the other hand, acetic acid with a higher polarity, as compared to acetic acid, does not have a tendency to co-dissolve water and phospholipids in the oil phase. Higher amount of organic acid may facilitate better reaction of wet gums but will result in higher moisture content in the oil phase. Therefore, based upon the phospholipid content, the amount of organic acid has to be optimized in order to get a higher oil yield with low moisture content in the oil phase. It was hypothesized that combination of organic acid and other favorable solvent might increase oil yield as well as reduce moisture in the oil phase. In order to verify the hypothesis diluted propionic acid, glycerin, phosphoric acid, propylene glycol, methanol, vinegar, oleic acid, acid oil and fusel oil were used as solvents. Out of all the solvent glycerin had oil yield that is comparable to addition of organic acid. As shown before addition of glycerin decreased emulsion viscosity and increased flowability, therefore glycerin was used as a solvent in combination with propionic acid for further study. As shown in Table 5, the combination of glycerin and propionic/acetic acid although slightly reduced the oil yield produced high quality oil low moisture. Glycerin helps in not only reducing the viscosity of the gums but, due to its high polarity, also reduces the moisture and phospholipids from the oil phase. Hydrochloric acid performed similar to sulfuric acid during hydrolysis.

TABLE 15

Chemical hydrolysis of wet gums

| No | Treatment | End pH | 8 hour settling Oil % | 8 hour settling Emulsion % | 8 hour settling Water % | Moisture in oil phase, % |
|---|---|---|---|---|---|---|
| 1 | Wet gums control | 4.0 | No separation occurred | | | |
| 2 | Wet gums + Sulfuric acid (SA) | 1.43 | 42 | 58 (Emulsion & water coagulated) | | 0.23 |
| 3 | Wet gums + 10% Propionic Acid (PA) + SA | 2.58 | 58 | 9 | 33 | 14.4 |
| 4 | Wet gums + 5% PA + SA | 1.89 | 48 | 16 | 36 | 3.61 |
| 5 | Wet gums + 10% Acetic Acid (AA) | 1.70 | 65 | 6 | 29 | 4.60 |
| 6 | Wet gums + 10% PA + Hydrochloric acid (HCl) | 1.8 | 54 | 3 | 43 | 7.54 |
| 7 | Wet gums + 10% AA + HCl | 1.72 | 49 | 11 | 41 | 1.79 |
| 8 | Wet gums + 20% Glycerin (GLY) + SA | 1.9 | 36 | 42 | 22 | |
| 9 | Wet gums + 10% GLY + 5% PA + SA | 1.84 | 44 | 22 | 34 | 1.49 |

Mass Balance Study for Chemical Hydrolysis of Wet Gums

Based on the above results mass balance study is performed on three different treatments of wet gums. In 400 g wet gum, calculated amount of propionic acid and 50% glycerin solution was added. The contents were mixed thoroughly and hydrolyzed with sulfuric acid to pH of 1.5-2. Table 6 shows the mass balance of different treatments.

TABLE 16

Mass balance of wet gums hydrolysis with different solvent treatments

| Fraction | Fraction wt. (g) | Moisture (%) | TFA (%) | TFA (g) | TFA Yield (%) |
|---|---|---|---|---|---|
| a) Hydrolysis using 10% propionic acid and sulfuric acid | | | | | |
| Oil | 220 | 14.4 | 79.6 | 175 | 99.4 |
| Emulsion | 20 | 37.2 | | | |
| Water | 180 | 58.7 | | | |
| b) Hydrolysis using 5% propionic acid, 10% glycerin and sulfuric acid | | | | | |
| Oil | 170 | 5.8 | 90.1 | 153.2 | 87 |
| Emulsion | 70 | 24.3 | | | |
| Water | 230 | 57.8 | | | |
| c) Hydrolysis using with 20% glycerin and sulfuric acid | | | | | |
| Oil | 130 | 1.2 | 98.4 | 127.9 | 72.7 |
| Emulsion | 150 | | | | |
| Water | 210 | | | | |

Note:
Treatments (a) and (b) may contain some residual propionic acid entrained in the oil phase.
Weight of wet gums = 400 g,
Theoretical TFA = 176 g Two Stage Chemical Hydrolysis of Wet Gums:

As an alternate processing method, wet gums were processed in two stages. In the first stage, wet gums are heated to 80° C. and thoroughly mixed with 10% wt propionic acid. Propionic acid addition to wet gums not only changed its viscosity and flowability but also reduced the pH to about 3, thereby partially hydrolyzing the phospholipids. The resulting wet gums mixture is dewatered by passing through a centrifuge. The water had lower salt content and lower organic content making it easy to handle/treat. In the second stage, the lipid phase is heated and sulfuric acid is added to complete the hydrolysis process. Due to the lower volume and lower pH of the material the amount of sulfuric acid required to complete the hydrolysis step is less. The final reaction mixture is allowed to settle in an oven at 80° C. High oil yield was observed with very little fallout. Moisture in the oil phase was lower (5.5%) than that from single stage process (14.4%). Therefore, two-stage process can be an alternative option other than traditional single stage hydrolysis process for better oil yield with lower moisture and AI content.

Chemical Hydrolysis of Dry Gums

Dry gums, unless the properties of the gums are being altered during the drying process, should essentially result in similar reaction yields upon chemical hydrolysis. Table 7 shows that addition of organic acids and/or glycerin as solvents to dry gums showed oil yields as similar to wet gums. Moreover, hydrochloric acid and sulfuric acid has similar effect during hydrolysis reaction.

TABLE 17

Chemical Hydrolysis of Dry Gums

| No | Treatment | End pH | 8 hour settling Oil % | 8 hour settling Emulsion % | Moisture in oil phase, % |
|---|---|---|---|---|---|
| 1 | Dry gums + SA | 1.52 | Little oil layer, lots of fallout | | |
| 2 | Dry gums + 10% PA + SA | 1.57 | 72 | 28 (fallout) | 2.66 |
| 3 | Dry gums + 10% PA + HCl | 1.67 | 66 | 34 (fallout) | 5.86 |
| 4 | Dry gums + 10% AA + HCl | 1.80 | 44 | 56 (fallout) | 2.75 |
| 5 | Dry gums + 20% GLY + SA | 1.49 | 52 | 48 (fallout) | |

Processing Wet Gums and Dry Gums Combination

Combination of 50% wet gum and a 50% dry gum was made and hydrolyzed using propionic acid as solvent. According to Table 8, the combination of wet gums and dry gums showed best result with addition of 10% propionic acid. Addition of 10% acetic acid gave the same result.

TABLE 18

Hydrolysis of Dry gums/Wet Gums combinations

| Treatment | End pH | Oil % | 8 hour settling | | Moisture in oil phase, % |
|---|---|---|---|---|---|
| | | | Emulsion % | Water % | |
| Wet gums + Dry gums + SA | 1.38 | 43 | 57 (fallout) | | 0.76 |
| Wet gums + Dry gums + 10% PA + SA | 1.55 | 66 | 3 | 32 | 10.22 |
| Wet gums + Dry gums + 10% AA + SA | 1.51 | 66 | 3 | 32 | 7.21 |

C. Option 3: Liquid Feed/Mold Inhibitor Product by Combining with Organic Acids

Wet gums, although nutritionally desirable, find limited application in feed due to their handling and storage difficulties. Organic acids, like propionic acid, besides being an excellent mold inhibitors overcomes these problems of gums. Development of such a product may offer a cost effective and more nutritious feed additive to improve shelf life of feed, high moisture grain/grain products from ethanol, and silage to name a few. In this study wet gums and propionic acid were mixed and judged for flowability and pourability. The propionic acid was neutralized to pH 5.2 using ammonium hydroxide. The following mixture was made:

73% Wet gums, 20% propionic acid, 7% NH$_4$OH

Initial flowability of the wet gums alone was like pudding. Adding propionic acid lead to an increase in flowability, moving much like water.

After neutralization with NH$_4$OH, the flowability remained high, becoming only slightly less flowable.

Propionic acid plays a dual role in the wet gums. Firstly, it makes the wet gums more flowable and easily pumped. Secondly, it acts as a preservative. Propionic acid acts as an effective preservative at the 0.02% level. The ratio of propionic acid in the liquid blend must be high enough so that when added to feed it will be present at a 0.02% level.

Option 4: Dry Feed Product by Combining with Agricultural Co-Products

It was identified that new feed products can be developed by mixing wet gums with specific feed ingredients including soy meal, corn gluten meal, vegetable oil, soy hulls, dried distiller grains etc. The dry ingredients were previously ground into flour using a blender before they are mixed with wet gums. The calcium oxide (CaO) and o-phosphoric acid play dual roles as both drying agents and as sources of nutrition. It is important for the dry blend to have low moisture content because moisture content is most critical for preservation.

Given below are some formulations of new feed products:

65% soybean meal flour, 35% enzymatic wet gums: The soybean meal flour and wet gums were mixed thoroughly and then dried in a 60° C. oven for eight hours. The initial moisture was 15.23% and the final moisture after heating was 5.48%. This product was balled up and oily. It was not free moving. This product contained 0.56% choline, 0.32% ethanolamine and 0.35% inositol, respectively.

62% soybean meal flour, 3% CaO, 33% enzymatic wet gums, 2% (85% a-phosphoric acid): Firstly, the CaO was mixed with the soybean meal flour. Secondly, the phosphoric acid was added to the wet gums. After preparing both the soybean meal flour and wet gum mixtures independently, the mixtures were added together and mixed thoroughly. The mixture was then dried in a 60° C. oven for eight hours. The initial moisture was 15.75% and the final moisture after heating was 3.98%. This mixture appeared less oily compared to the first mixture without any drying agents. It was free moving with balled up pieces. This product contained 0.53% choline, 0.3% ethanolamine and 0.33% inositol, respectively.

59% soybean meal flour, 4.5% CaO, 32% enzymatic wet gums, 4.5% a-phosphoric acid: Firstly, the CaO was mixed with the soybean meal flour. Secondly, the phosphoric acid was added to the wet gums. After preparing both the soybean meal flour and wet gum mixtures independently, the mixtures were added together and mixed thoroughly. The mixture was then dried in a 60° C. oven for eight hours. The initial moisture was 16.74% and the final moisture after heating was 3.31%. This mixture appeared less oily compared to the first mixture without any drying agents. In addition, it was free moving with scant balled up pieces. This product contained 0.51% choline, 0.29% ethanolamine and 0.32% inositol, respectively.

60% soybean meal flour, 5% CaO, 30% enzymatic wet gums, 5% phosphoric acid: Firstly, the CaO was mixed with the soybean meal flour. Secondly, the phosphoric acid was added to the wet gums. After preparing both the soybean meal flour and wet gum mixtures independently, the mixtures were added together and mixed thoroughly. Mixture warmed when two mixtures were combined. Final temperature was 36° C. Before drying the soybean meal flour and wet gums feel oily to the touch and can be easily molded into pieces that stay together. The mixture was then dried in a 60° C. oven for eight hours. The initial moisture was 16.13% and the final moisture after heating was 2.97%. The pH was 7.26. The final product was free flowing. This product contained 0.48% choline, 0.27% ethanolamine and 0.3% inositol, respectively.

60% corn gluten meal, 5% CaO, 30% enzymatic wet gums, 5% phosphoric acid: Firstly, the CaO was mixed with the corn gluten meal. Secondly, the phosphoric acid was added to the wet gums. After preparing both the corn gluten meal and wet gum mixtures independently, the mixtures were added together and mixed thoroughly. Mixture warmed when two mixtures were combined. Final temperature was 37° C. Before drying the corn gluten meal and wet gum mixture is very fine and movable, like sand that is slightly moist. The mixture cannot readily be molded into pieces. If pieces are formed they crumble easily. The mixture was then dried in a 60° C. oven for eight hours. The initial moisture was 16.10% and the final moisture after heating was 2.45%. The pH was 6.95. The final product was free flowing. This product contained 0.48% choline, 0.27% ethanolamine and 0.3% inositol, respectively.

60% Distillers dried grains, 5% CaO, 30% enzymatic wet gums, 5% phosphoric acid: Firstly, the CaO was mixed with the distillers dried grains (DDG) flour. Secondly, the phosphoric acid was added to the wet gums. After preparing both the DDG flour and wet gum mixtures independently, the mixtures were added together and mixed thoroughly. Initial temperature of the DDG mixture was 29° C. and the wet gums mixture was 24° C. When combined the temperature warmed to 38° C. Before drying the DDG mixture was clumpy and sticky and not freely moving. It balled easily into large clumps and did not break apart readily. The mixture was then dried in a 60° C. oven for eight hours. The initial moisture was 16.77% and the final moisture after heating was 3.09%. The pH was 6.78. The final product was free flowing. This product contained 0.48% choline, 0.27% ethanolamine and 0.3% inositol, respectively.

Accordingly, enzymes are able to hydrolyze soapstock/wet gums and produce clear oil, reduce the emulsion and release clear water. Other major outcome of this study is that the proteases were also able to hydrolyze soapstock at neutral pH. Phospholipase A2 worked effectively than others. Post centrifugation should be considered to obtain better oil yield and reduce emulsion.

The present invention shows that wet gum, dry gum with high phospholipid content, can be successfully hydrolyzed with high oil yields both by chemical and enzymatic processing. Enzymes can selectively hydrolyze the phospholipids to release free fatty acids. The addition of solvents such as propionic acid and glycerin considerably increased the oil yield. Mass balance studies showed similar results to small scale experiments. Some other options like drying process or blending with other agricultural co-products may also have good commercial value.

In addition to fatty acids, the phospholipids subjected to the hydrolysis reaction contain further valuable components. These components separate into the water phase created by the hydrolysis reaction, while the above-described fatty acids are located in the fatty-acid-rich oil phase. Methods of processing and concentrating these further components are provided. These methods are applicable to phospholipids of all types, and not just those resulting from the enzymatic processing discussed above. Gums or phospholipids subjected to other types of hydrolysis, such as physical methods, may also be processed according the methods described herein. In one aspect of the invention, a process for delivering nitrogenous materials such as choline, ethanolamine, inositol and serine as feed or food supplements by suspending degumming byproducts in a lipid medium is disclosed. Further disclosed is a process where these degumming byproducts are concentrated to enrich one or more of choline, ethanolamine, inositol and serine.

As discussed above, degumming byproducts are typically highly viscous and non-homogenous making them difficult to handle. It is further challenging to transform these byproducts into uniform feed and food products. Being in the similar class of compounds, lipids (fats and oils) can generally be considered as good carriers for such byproducts. However, due to their amphiphilic nature and presence of other non-lipid impurities, degumming byproducts have limited solubility in lipids and tend to separate into another layer.

It is common practice to use emulsifiers to suspend hydrophilic and hydrophobic materials with each other at various ratios. However, it is uncommon to suspend a significant quantity of amphiphilic material with hydrophobic or hydrophilic materials. Several commercially available emulsifiers were tested in the lab to be unsatisfactory. Accordingly, a novel approach is used to overcome this issue. In this approach, the byproducts are first mixed with an oil and a viscosity modifier. Further to this mixture, a dilute alkali is added slowly while the entire contents are homogenized inducing a carefully controlled chemical reaction of alkali with free fatty acids to form fatty acid salts. The pH range of this mixture is 5-6, where most of the phospholipid components are soluble. This mixture upon settling or centrifugation separates into two layers. The resulting top layer is a flowable, homogenous material containing nitrogenous compounds such as choline, ethanolamine, serine and inositol.

In an attempt to further increase the concentration of the nitrogenous compounds, the degumming byproducts are further processed. In this process, in the presence of water and acid catalyst, the phospholipid molecule, present in the byproduct feedstocks, breaks at various positions (Sn1 to Sn4) depending on the degree of hydrolysis. If one fatty acid is cleaved, a lysophospolipid results having one fatty acid attached to the glycerol. If both fatty acids are cleaved, a glycerophospholipid results. For example, as shown in FIG. 1, the phosphatidyl choline molecule has two fatty acid chains and a phosphatide group attached to a glycerol backbone. Hydrolysis may lead to lysophospatidylcholine having one fatty acid molecule, glycerophosphorylcholine having no fatty acid chain, or phosphocholine having only the phosphate and choline polar head group, depending on the degree of hydrolysis. Similar results occur for all phospholipids, but with a different compound attached to the phosphate group, for example, choline, inositol, ethanolamine, and others.

Lecithin is 100% hexane soluble and, therefore, does not mix well with water, which is essential for hydrolysis process. Hence, a low concentration of alcohol was added as a fluidizer to aid the hydrolysis process. Alcohol also enhances separation between oil and water soluble phases after the completion of hydrolysis. The alcohols chosen for this purpose were isopropanol, ethanol and methanol which are low carbon alcohols. In one example, isopropanol at 20-30% concentration and at a ratio of 2:1 on weight basis to Lecithin behaved as an excellent fluidizer and aided in hydrolysis. For ethanol, a concentration of 20-30% was sufficient, but at a ratio ranging between 3:1 to 5:1 on weight basis to these feed stocks. Methanol is best used at the same concentration as well but at a higher ratio ranging from 8:1 to 10:1 of the weight of the feedstock. Sulfuric acid was used as the catalyst to promote hydrolysis.

In an exemplary embodiment of the hydrolysis reaction, feedstock is mixed with the required ratio of aqueous alcohol mixture in a reaction vessel. 2-4% by weight of concentrated sulfuric acid may be used as a catalyst. The reaction may be carried out at 70-80° C. for 3-5 hours to ensure complete hydrolysis. After hydrolysis, the reacted contents were transferred to a separatory funnel and settled for 18-24 h at a temperature of 80° C. to ensure complete separation of oil and water soluble fractions.

The invention is further described with the following examples, which should not be construed as limiting.

Example 1

In a 400 mL beaker, 80 g of VOP were added to 120 g of acid oil at 150° F. and mixed at 100 RPM for 30 minutes while maintaining temperature at 150° F. thereby ensuring uniformity. After mixing, the contents were settled at 150° F. for 24 hours. The contents separated into a fluid phase on the top and slurry like fallout in the bottom. The total weight of the top and bottom phase was recorded 153 g and 46.4 g, respectively. The top phase collected as the final blend product contained 0.5% choline.

Example 2

In a 400 mL beaker, 100 g of lecithin was added to 100 g of acid oil at 150° F. and mixed at 100 RPM for 30 minutes thereby ensuring uniformity. 2.0 g of glycerin and 5 mL of 25% sodium hydroxide were mixed in a separate beaker and this alkaline glycerin was added to the oil mixture while mixing for another 20 minutes. The mixture was then homogenized at 16,000 RPM for 3 minutes while maintaining temperature at 150° F. After homogenization the contents were settled at 150° F. for 24 hours. The contents separated into a fluid phase on the top and slurry like fallout in the bottom. The total weight of the top and bottom phase was recorded 160 g and 40 g. respectively. The top phase collected as the final blend product contained 1.2% choline.

Example 3

100 g of lecithin was hydrolyzed with 200 g of 30% concentration isopropanol, thereby ensuring a 2:1 ratio. 2.5 g of concentrated sulfuric acid was added as a catalyst (2.5% by weight of lecithin taken). The reaction was carried out at 80° C. for 3 hours. After the reaction, the contents were transferred to a separatory funnel and settled at 75° C. for 5 hours. The contents separated into an oil phase on the top, an emulsion layer in the middle and a water layer on the bottom. The emulsion and water layers were collected together. The final distribution of oil phase and Emulsion+Water phases was 65 g and 35 g respectively. The Emulsion+Water phases were concentrated using a rotary evaporator and the final product analyzed for choline content. Choline concentration in the original Lecithin feedstock was 2.88% and in the final product was 5.7%

Example 4

100 g of lecithin was hydrolyzed with 300 g of 30% concentration ethanol ensuring a 3:1 ratio. 4 g of concentrated sulfuric acid was added as a catalyst (4% by weight of lecithin taken). The reaction was carried out at 75° C. for 3 hours. After the reaction, the contents were transferred to the separatory funnel and settled at 75° C. for 5 hours. The contents separated into an oil phase on the top, an emulsion layer in the middle and a water layer on the bottom. The emulsion and water layers were collected together. The final distribution 60 g in the oil phase and emulsion plus water phases were 40 g on a dry basis. The Emulsion+Water phases were concentrated using a rotary evaporator and the final product analyzed for choline content. Choline concentration in the original Lecithin feedstock was 2.88% and in the final product was 5.8%

Example 5

100 g of VOP were hydrolyzed with 1000 g of 30% concentration Isopropanol thereby ensuring a 10:1 ratio. 4 g of concentrated sulfuric acid was added as a catalyst (4% by weight of VOP taken). The reaction was carried out at 80° C. for 3 hours. After the reaction, the contents were transferred to the separatory funnel and settled at 75° C. for 12 hours. The contents separated into an oil phase on the top, an emulsion layer in the middle and a water layer in the bottom. The emulsion and water layers were collected together. The final distribution of oil phase and Emulsion+Water phases was 70 g and 30 g respectively. The Emulsion+Water phases were concentrated using rotary evaporator, and the final product analyzed for choline content. Choline concentration in the original VOP feedstock was 2.43% and in the final product was 5.09%

Example 6

100 g of VOP were hydrolyzed with 1000 g of 30% concentration ethanol thereby ensuring a 10:1 ratio. 4 g of concentrated sulfuric acid were added as a catalyst (4% by weight of VOP taken). The reaction was carried out at 80° C. for 3 hours. After the reaction, the contents were transferred to the separatory funnel and settled at 75° C. for 12 hours. The contents separated into an oil phase on the top, an emulsion layer in the middle and a water layer in the bottom. The emulsion and water layers were collected together. The final distribution of oil phase and Emulsion+Water phases was 65-70 g and 30-35 g respectively. The Emulsion+Water phases were concentrated using rotary evaporator and the final product analyzed for choline content. Choline concentration in the original VOP feedstock was 2.43% and in the final product was between 5-6%

Example 7

100 g of enzymatic wet gums were hydrolyzed with 200 g of 100% concentration Isopropanol thereby ensuring 2:1 ratio. 4 g of concentrated sulfuric acid were added as a catalyst (4% by weight of VOP taken). The reaction was carried out at 70° C. for 3 hours. After the reaction, the contents were transferred to the separatory funnel and settled at 75° C. for 2 hours. The contents separated into a solvent phase on the top and water phase on the bottom. Employing distillation, the solvent phase yielded oil and emulsion phases. The emulsion and water phases were collected together. The final distribution of oil phase and Emulsion+Water phases was 53 g and 47 g respectively. The Emulsion+Water phases were concentrated using rotary evaporator and the final product analyzed for choline content. Choline concentration in the original wet gum feedstock was 3.25% and in the final product was 7.3%

Example 8

143 g of water phase from the process described in example 3 was treated with alcohol in a 1:1 ratio with the reaction mixture adjusted to pH 9. Two phases were observed upon settling, the alcohol phase stays at the top and the residue at the bottom. The top alcohol phase was collected and filtered through a 20 micron filter paper. Both permeate and retentate were collected and dried. 4 g of filtrate and 16 g residue were obtained on dry basis.

The initial choline concentration in the water was 5.7%.
The choline concentration in the permeate was 16.94%
The choline concentration in the retentate phase was 1.2%

Example 9

900 g of enzymatic wet gums were hydrolyzed using 13.5 g of concentrated sulfuric acid as catalyst. The reaction was performed in a pressurized reactor for 10 minutes at 150° C., 120 Psig and 400 rpm mixing speed. The products obtained were 300 g oil, 361 g water, and 239 g emulsion. The water phase was concentrated using the rotary evaporator and the final product analyzed for choline and inositol content. The process described in this example can be performed using alcohols such as methanol, ethanol and isopropanol to obtain higher yield of choline in the final product.

The initial choline concentration in the wet gums was 3.25%
The choline concentration in the water phase was 6.2%
The initial inositol concentration in the wet gums was 2.03%
The inositol concentration in water phase was 2.7%

Although various representative embodiments of this invention have been described above with a certain degree of particularity, those skilled in the art could make numerous alterations to the disclosed embodiments without departing from the spirit or scope of the inventive subject matter set forth in the specification and claims. Joinder references (e.g. attached, adhered, joined) are to be construed broadly and may include intermediate members between a connection of elements and relative movement between elements. As such, joinder references do not necessarily infer that two elements are directly connected and in fixed relation to each other. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to the embodiments outlined above, various alternatives, modifications, variations, improvements and/or substantial equivalents, whether known or that are or may be presently foreseen, may become apparent to those having at least ordinary skill in the art. Listing the steps of a method in a certain order does not constitute any limitation on the order of the steps of the method. Accordingly, the embodiments of the invention set forth above are intended to be illustrative, not limiting. Persons skilled in the art will recognize that changes may be made in form and detail without departing from the spirit and scope of the invention. Therefore, the invention is intended to embrace all known or earlier developed alternatives, modifications, variations, improvements, and/or substantial equivalents.

The invention claimed is:

1. A method of processing a gum feedstock comprising at least one phospholipid material that comprises at least one nitrogen-based material, comprising:
   hydrolyzing said feedstock with an acid catalyst in the presence of an alcoholic solvent to form a first phase and a second phase, said first phase comprising oil and said second phase comprising phospholipid material containing at least one nitrogen-based material; and
   further concentrating said nitrogen-based material from the second phase;
   wherein said gum feedstock is selected from the group consisting of wet gums, dried gums, enzymatic wet gums, lecithin, and vegetable oil phospholipids.

2. The method of claim 1 wherein said acid catalyst is sulfuric acid.

3. The method of claim 1 wherein said alcoholic solvent is selected from the group consisting of methanol, ethanol, isopropanol and butanol.

4. The method of claim 3 wherein said first phase further comprises said alcohol.

5. The method of claim 4 wherein said second phase further comprises water and said alcohol.

6. The method of claim 5 further comprising separating water and alcohol from said second phase prior to further concentrating said nitrogen-based material.

7. The method of claim 6 wherein said second phase is dried to recover said water and alcohol.

8. The method of claim 7 wherein said nitrogen-based material is fractionated.

9. The method of claim 7 further comprising: treating said dried second phase with alcohol to form an alcohol phase and a residue phase; filtering said alcohol phase to create a permeate and a retentate; and concentrating said nitrogen-based material from at least one of said permeate and said retentate.

10. The method of claim 9 wherein said filtering step comprises filtering said alcohol phase through filter paper.

11. The method of claim 1 wherein hydrolyzing said feedstock also results in an emulsion phase.

12. The method of claim 11 wherein said second and emulsion phases are combined prior to further concentrating said nitrogen-based material.

13. A method of processing a gum feedstock comprising at least one phospholipid material that comprises at least one nitrogen-based material, comprising:
   obtaining said feedstock, wherein said feedstock is a byproduct of vegetable oil refining selected from the group consisting of wet gums, dried gums, enzymatic wet gums, lecithin, and vegetable oil phospholipids;
   hydrolyzing said phospholipid materials with a catalyst in the presence of an alcoholic solvent selected from the group consisting of methanol, ethanol, isopropanol and butanol, to form a first phase and a second phase, said first phase comprising oil and said second phase comprising phospholipid material containing at least one nitrogen-based material, water, and said alcohol, wherein said catalyst is an enzyme or an acid;
   separating said first and second phases; and
   further concentrating said nitrogen-based material from the second phase.

14. The method of claim 13 wherein hydrolyzing said phospholipid materials also results in an emulsion phase.

15. The method of claim 14, wherein said second and emulsion layers are combined prior to further concentrating said nitrogen-based material.

16. The method of claim 13 wherein said water and alcohol are separated from said second phase prior to further concentrating said nitrogen-based material.

17. The method of claim 16 wherein said nitrogen-based material is fractionated.

18. The method of claim 17 further comprising:
   treating said second phase with alcohol to form an alcohol phase and a residue phase;
   filtering said alcohol phase to create a permeate and a retentate; and
   concentrating said nitrogen-based material from at least one of said permeate and said retentate.

* * * * *